US012390073B2

(12) United States Patent
Xu et al.

(10) Patent No.: US 12,390,073 B2
(45) Date of Patent: Aug. 19, 2025

(54) BASE STATION AND CLEANING SYSTEM

(71) Applicant: Anker Innovations Technology Co., Ltd., Changsha (CN)

(72) Inventors: Ziyang Xu, Changsha (CN); Xiaoqing Sang, Changsha (CN)

(73) Assignee: Anker Innovations Technology Co., Ltd., Changsha (CN)

( * ) Notice: Subject to any disclaimer, the term of this patent is extended or adjusted under 35 U.S.C. 154(b) by 312 days.

(21) Appl. No.: 18/135,403

(22) Filed: Apr. 17, 2023

(65) Prior Publication Data

US 2023/0329513 A1    Oct. 19, 2023

(30) Foreign Application Priority Data

Apr. 19, 2022   (CN) ......................... 202210413959.2

(51) Int. Cl.
*A47L 11/40* (2006.01)
*A47L 11/00* (2006.01)
(Continued)

(52) U.S. Cl.
CPC ........... *A47L 11/4091* (2013.01); *A47L 11/00* (2013.01); *A47L 11/24* (2013.01); *A47L 11/28* (2013.01);
(Continued)

(58) Field of Classification Search
CPC ............. A47L 11/4091; A47L 11/4083; A47L 2201/026; A47L 2201/028; A47L 11/24; A47L 11/4011; A47L 2201/024; A47L 11/00; A47L 11/28; A47L 11/40; A47L 11/408; A47L 11/4088; A61L 2/18;
(Continued)

(56) References Cited

U.S. PATENT DOCUMENTS

2019/0290089 A1 *   9/2019   Johnson ............... A47L 11/4013
2020/0069136 A1 *   3/2020   Sasaki ..................... A47L 11/30

FOREIGN PATENT DOCUMENTS

CN        113080779 A   *   7/2021   ............... A47L 1/02
CN        113331746 A   *   9/2021
(Continued)

OTHER PUBLICATIONS

CN214906356 translation (Year: 2021).*
(Continued)

*Primary Examiner* — Michael E Barr
*Assistant Examiner* — Lauren G Orta (57) ABSTRACT

Disclosed is a base station comprising a base and a liquid path system disposed on the base. The liquid path system may comprise a first device and a second device. The first device may be configured to perform a first treatment on water to form a first liquid, and the second device is configured to perform a second treatment on water to form a second liquid. The second liquid may be different from the first liquid in temperature and/or composition. The first device can provide the first liquid with a first function for a cleaning robot, and the second device can provide a second liquid with a second function for the cleaning robot, so that the base station can provide a variety of liquids with different functions for the cleaning robot to meet different floors, different environments, and different user needs.

17 Claims, 6 Drawing Sheets

(51) Int. Cl.
  *A47L 11/24* (2006.01)
  *A47L 11/28* (2006.01)
  *A61L 2/18* (2006.01)
  *A61L 2/26* (2006.01)
  *B08B 3/08* (2006.01)
  *B08B 3/10* (2006.01)
  *B08B 13/00* (2006.01)

(52) U.S. Cl.
  CPC .......... *A47L 11/40* (2013.01); *A47L 11/4011* (2013.01); *A47L 11/408* (2013.01); *A47L 11/4083* (2013.01); *A47L 11/4088* (2013.01); *A61L 2/18* (2013.01); *A61L 2/26* (2013.01); *B08B 3/08* (2013.01); *B08B 3/10* (2013.01); *B08B 13/00* (2013.01); *A47L 2201/024* (2013.01); *A47L 2201/026* (2013.01); *A47L 2201/028* (2013.01); *A61L 2202/17* (2013.01); *B08B 2203/007* (2013.01)

(58) Field of Classification Search
  CPC ......... A61L 2/26; A61L 2202/17; B08B 3/08; B08B 3/10; B08B 13/00; B08B 2203/007
  See application file for complete search history.

(56) References Cited

FOREIGN PATENT DOCUMENTS

| CN | 113455968 A | * 10/2021 | |
|---|---|---|---|
| CN | 214906356 U | * 11/2021 | |
| CN | 215191318 U | * 12/2021 | .............. A47L 11/40 |

OTHER PUBLICATIONS

CN113080779 translation (Year: 2021).*
CN113331746 translation (Year: 2021).*
CN113455968 translation (Year: 2021).*
CN215191318 translation (Year: 2021).*
Dec. 28, 2023—(CN) First Office Action—App. No. 2022104139592 w/ Machine Translation.

* cited by examiner

BASE STATION AND CLEANING SYSTEM

CROSS-REFERENCE TO RELATED APPLICATION

This application claims priority to CN application No. 202210413959.2, filed on Apr. 19, 2022. The entire content of the prior application is incorporated herein by reference.

FIELD

The present disclosure relates to the technical field of cleaning, in particular to a base station and a cleaning system.

BACKGROUND

When mopping a floor, a cleaning robot often needs to wet a mop or wet the floor to achieve a better cleaning effect. Liquid in a water tank of the cleaning robot needs to be replenished after consumption, so the cleaning robot needs to be used together with a base station. The base station contains a water tank whereby fluid in the tank may be pumped out to refill the water tank of the cleaning robot or to clean the mop of the cleaning robot.

SUMMARY

The disclosure provides a base station and a cleaning system which can provide a variety of liquids with different functions for a cleaning robot (e.g., device) to meet different floors, different environments, and different user needs.

The disclosure provides a base station comprising a base and a liquid path structure (e.g., system) arranged on the base. The liquid path structure may comprise: a first functional mechanism having a first functional module configured to perform a first treatment on water to form a first liquid; and a second functional mechanism having a second functional module configured to perform a second treatment on water to form a second liquid, and the second liquid is different from the first liquid in temperature and/or composition.

The liquid path structure may further comprise a drainage channel selectively communicating with the first functional mechanism and the second functional mechanism and configured to communicate with a clean water tank of a cleaning robot and/or a cleaning tank of the base station. The liquid in the first functional mechanism can be discharged through the drainage channel, and the liquid in the second functional mechanism can also be discharged through the drainage channel. The communication between various components of the present disclosure may comprise physical and/or electronic connection.

The liquid path structure may further comprise: a first liquid outlet pipe communicating with the first functional mechanism and selectively communicating with the drainage channel: a second liquid outlet pipe communicating with the second functional mechanism and selectively communicating with the drainage channel; and a first gate connected with the first liquid outlet pipe, the second liquid outlet pipe and the drainage channel and configured to control connection between the first liquid outlet pipe and the drainage channel and control connection between the second liquid outlet pipe and the drainage channel. The first liquid outlet pipe may be configured to discharge the liquid in the first functional mechanism, and when the first liquid outlet pipe communicates with the drainage channel, the first functional mechanism communicates with the drainage channel. The second liquid outlet pipe may be configured to discharge the liquid in the second functional mechanism, and when the second liquid outlet pipe communicates with the drainage channel, the second functional mechanism communicates with the drainage channel. By connecting the first liquid outlet pipe and the second liquid outlet pipe with the drainage channel, the liquid in the first functional mechanism and the liquid in the second functional mechanism can be discharged simultaneously or separately.

The liquid path structure may further comprise: a first water inlet pipe communicating with the first functional mechanism: a second water inlet pipe communicating with the second functional mechanism: a water supply pipe selectively communicating with the first water inlet pipe and the second water inlet pipe and configured to provide the water for the first functional mechanism and the second functional mechanism; and a second gate connected with the water supply pipe, the first water inlet pipe, and the second water inlet pipe and configured to control connection between the water supply pipe and the first water inlet pipe and control connection between the water supply pipe and the second water inlet pipe. The water supply pipe can provide water for the first functional mechanism and the second functional mechanism to meet the requirements of the first functional mechanism and the second functional mechanism.

The first functional mechanism and the second functional mechanism may be connected in series, and the liquid path structure may further comprise: a third liquid outlet pipe communicating with the second functional mechanism and selectively communicating with the drainage channel. The first functional mechanism can be configured to perform the first treatment on water to form the first liquid, and can also be used as a water storage container without setting an additional water storage tank, thereby reducing the number of water tanks in the base station.

The liquid path structure may further comprise: a second functional water tank having a third cavity in which a functional liquid is stored. The functional liquid may be different from the first liquid and the second liquid in composition. A fourth liquid outlet pipe may communicate with the third cavity and selectively communicate with the drainage channel. The functional liquid needed by the cleaning robot can be pre-stored in the third cavity, and when the functional liquid in the third cavity is needed, the functional liquid in the third cavity may be introduced into the drainage channel through the fourth liquid outlet pipe. The functional liquid may comprise a cleaning liquid.

The liquid path structure may further comprise a water storage tank installed on the base and having a water storage cavity configured to store the liquid.

The first functional mechanism may have a first cavity, the second functional mechanism may have a second cavity, and the water storage cavity may selectively communicate with the first cavity and the second cavity. The water storage tank may be a mechanism independent from the first functional mechanism and the second functional mechanism, and can provide the liquid for the first cavity and the second cavity.

The water storage tank may comprise either of the first functional module and the second functional module. Besides the water storage function, the water storage tank can have a function of heating water or electrolyzing water, without additionally setting a water tank such as an electrolyzed water tank or a hot water tank in the base station.

The first functional module may comprise an electrolyzer configured to electrolyze the liquid; and the second functional module may comprise a heater configured to heat the liquid. The liquid may be electrolyzed by the electrolyzer to form electrolyzed water which can meet sterilization and disinfection needs of a user. The liquid may be heated by the heater to form hot water which can soften the stains, thus better removing stubborn stains on the floor.

The first functional mechanism may be provided with a first cavity and a first vent hole communicating with the first cavity. The second functional mechanism may be provided with a second cavity and a second vent hole communicating with the second cavity. The first vent hole can make the first cavity communicate with the atmosphere, thus preventing a siphon effect when the liquid in the first cavity is discharged through the drainage pipe; and the second vent hole can make the second cavity communicate with the atmosphere, thus preventing a siphon effect when the liquid in the second cavity is discharged through the drainage pipe.

The base station may further comprise a selector and a control module (e.g., a control circuit). The selector may be in communication connection with the control module and configured to accept selection operation and output selection information according to the selection operation, and the control module may be configured to control on/off of the first functional module and/or the second functional module according to the selection information. Or the base station may further comprise a control module configured to be in communication connection with a terminal and receive selection information sent by the terminal and control on/off of the first functional module and/or the second functional module according to the selection information. The user can realize full-automatic liquid path control through the control module, and the user can meet liquid needs of the cleaning robot with one key through a simple interactive interface.

The disclosure may provide a cleaning system comprising a cleaning robot and the base station configured to replenish or/and clean the cleaning robot.

The disclosure has the following advantages: the first functional mechanism of the base station can provide the first liquid with the first function, and the second functional mechanism can provide the second liquid with the second function, so that the base station can provide various liquids with different functions to meet different floors, different environments and different user needs. Meanwhile, the base station integrates a variety of liquid treatment functions, and liquid with multiple functions can be directly formed in the base station only by providing the liquid (e.g., water) for the base station without adding liquid to the base station, so that the base station has more functions, which can reduce labors of a user and improve user experience.

BRIEF DESCRIPTION OF THE DRAWINGS

In order to more clearly illustrate embodiments of the disclosure or technical solutions of the related art, drawings that need to be used in description of the embodiments or the related art are briefly introduced below, and it will be apparent that the drawings in the following description are only some embodiments of the disclosure, and other drawings may be obtained by those skilled in the art without inventive work based on these drawings.

REFERENCE NUMERALS

10: base: 20: liquid path structure: 211: first functional mechanism; 211a: first cavity: 212: second functional mechanism: 212a: second cavity: 213: second functional water tank: 213a: third cavity: 214: water storage tank: 214a: water storage cavity: 221: drainage channel: 222: first liquid outlet pipe: 223: second liquid outlet pipe: 224: first water inlet pipe: 225: second water inlet pipe: 226: water supply pipe: 227: third liquid outlet pipe: 228: fourth liquid outlet pipe: 231: first gate: 232: second gate: 233: third gate: 234: first valve: 235: second valve: 241: first driver: 242: second driver: 243: third driver: 250: cleaning robot: 251: first vent hole; 252: second vent hole.

DETAILED DESCRIPTION

In order to make the purpose, technical solutions and advantages of the disclosure clearer, the disclosure will be described in more detail with reference to the drawings. It should be understood that the examples or embodiments described herein are only used to explain the disclosure and are not used to limit the disclosure.

When mopping a floor, a cleaning robot often needs to wet a mop or wet the floor to achieve a better cleaning effect. The liquid in a water tank of the cleaning robot needs to be replenished after consumption, so the cleaning robot needs to be used together with a base station. The base station contains a water tank whereby fluid in the tank is pumped out to refill the water tank of the cleaning robot or to clean the mop of the cleaning robot.

However, the base station in the related art can only provide a single type of liquid for the cleaning robot, and the liquid needed to mop the floor is different for different floors, different environments, and/or different user needs. For example, if there is an oil stain on the floor, it will be better to mop the floor with a cleaning liquid that can remove the oil stain. As another example, if there is a stubborn stain on the floor, it may be necessary to soften the stain to mop the floor, and it is better to soften the stain with hot water. As another example, if there is a need for sterilization and disinfection, it is necessary to use disinfectant or electrolyzed water for disinfection.

The disclosure provides a base station and a cleaning system to solve the technical problem that the base station in the related art can only replenish a cleaning robot with a single kind of liquid.

Figure 1:
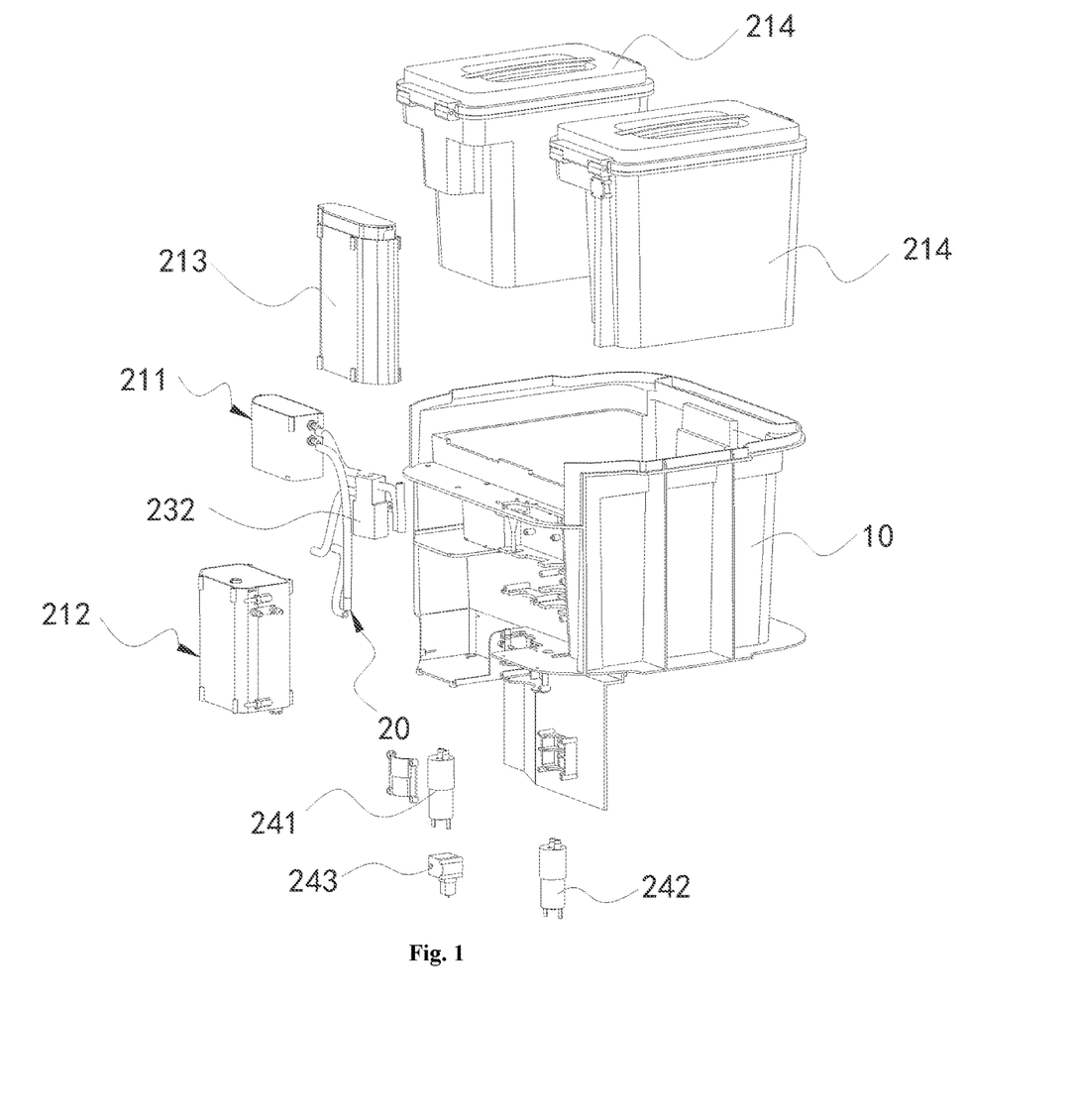
FIG. 1 is an exploded perspective view of a base station.
Figure 2:
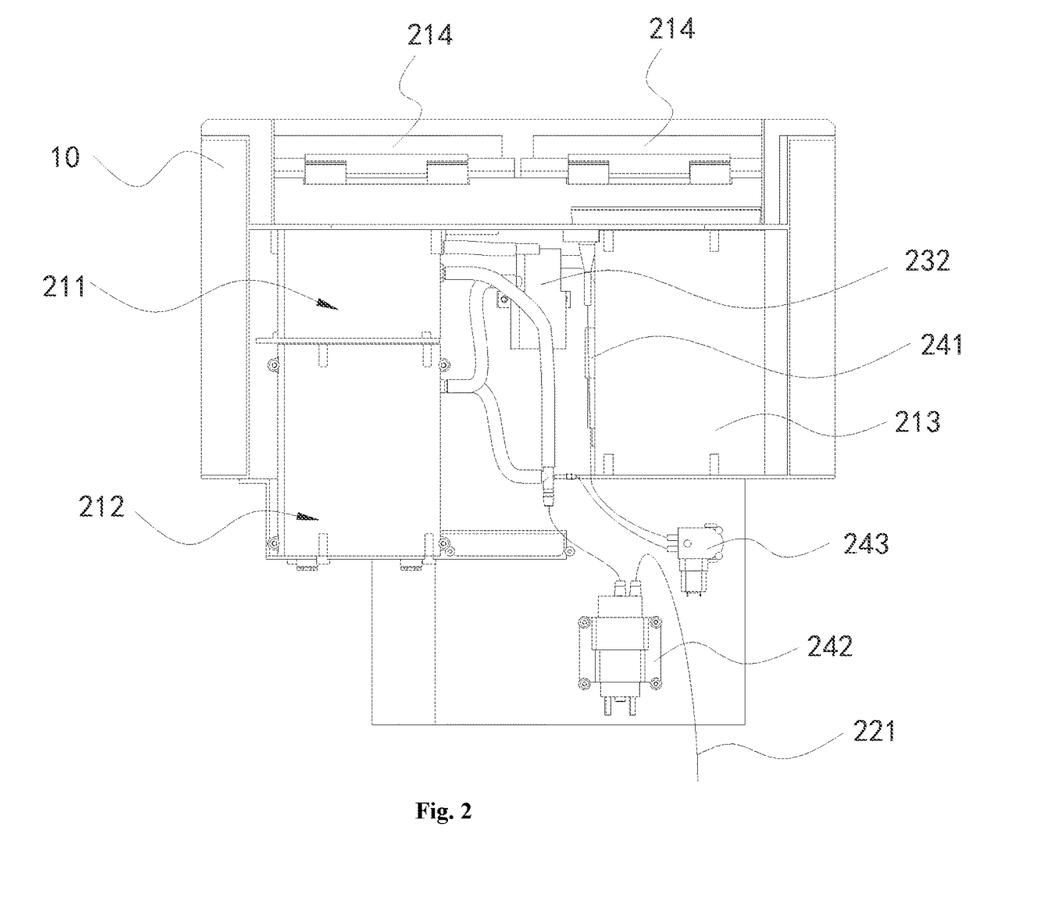
FIG. 2 is a front view of the base station.

A base station, as shown in FIGS. 1 and 2, may comprise a base 10 and a liquid path structure 20 (e.g., a channel) provided on the base 10, and the liquid path structure 20 can transport a liquid (e.g., water) and output liquids with multiple types and/or functions, so that a cleaning robot can be replenished (e.g., refilled) and/or cleaned to meet different floors, different environments, and different user needs. The liquid path structure 20 may fluidly connect the base 10 with a cleaning robot (e.g., a docked cleaning robot).

Figure 3:
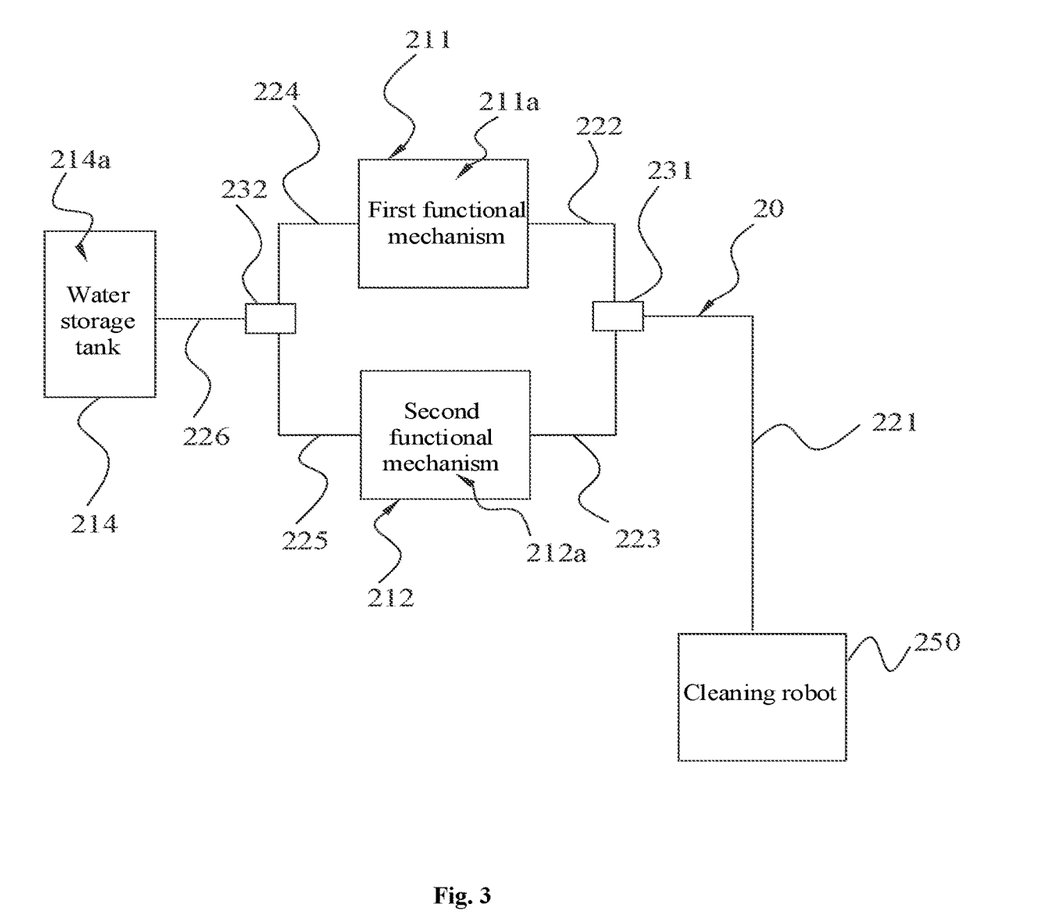
FIG. 3 shows a schematic diagram of a liquid path structure.

As shown in FIG. 3, the liquid path structure 20 may comprise a first functional mechanism 211 and a second functional mechanism 212. The first functional mechanism 211 (e.g., a first device) may have a first functional module configured to perform a first treatment on the liquid (e.g., water) to form a first liquid. The second functional mechanism 212 (e.g., a second device) may have a second functional module configured to perform a second treatment on the liquid to form a second liquid. The temperature and/or composition of the second liquid may be different from those of the first liquid.

It should be noted that the liquid may be clear water or other liquids. The substance of the second liquid may be different from that of the first liquid. For example, the first liquid may be hydrogen peroxide disinfectant and the second liquid may be soapy water. The substance of the second liquid may be the same as that of the first liquid, but a concentration of the substance of the second liquid may be different from that of the substance of the second liquid. For example, both the second liquid and the first liquid may be hydrogen peroxide disinfectant, but the concentration of the second liquid may be higher than that of the first liquid.

It can be understood that the first functional mechanism 211 can provide (e.g., generate) a first liquid with a first function for the cleaning robot, and the second functional mechanism 212 can provide a second liquid with a second function for the cleaning robot, so that the base station can provide a variety of liquids with different functions for the cleaning robot to meet different floors, different environments and different user needs. For example, if the first liquid is electrolyzed water and the second liquid is hot water, electrolyzed water has a disinfection function, which can meet a user need for sterilization and disinfection, and hot water can soften stains, which can better remove stubborn stains on the floor.

It should also be noted that the base station integrates a variety of liquid treatment functions, and liquid with multiple functions can be directly formed in the base station by providing water for the base station without adding the specific types of liquid to the base station, so that the base station has more functions, which can reduce labors of a user and improve user experience.

In an example, the first functional module may comprise an electrolyzer configured to electrolyze the liquid. It can be understood that the first liquid may be electrolyzed water. The liquid may be electrolyzed by the electrolyzer to form electrolyzed water, which can meet sterilization and disinfection needs of a user. The model and size of the electrolyzer can be selected according to actual needs, and are not specifically limited in the disclosure. Specific operating principles of an electrolyzer have been disclosed in the related art, and are not repeated in the disclosure.

The second functional module may comprise a heater (e.g., a heating tube) configured to heat the liquid. It can be understood that the second liquid may be hot water at this time. The liquid may be heated by the heater to form hot water which can soften stains, thus better removing stubborn stains on the floor. The heater may be an instant heating tube. The model and size of the instant heating tube can be selected according to actual needs, and are not specifically limited in the disclosure. Specific operating principles of a heater have been disclosed in the related art, and are not repeated in the disclosure. Other examples of the heater may comprise a heat storage heater.

It should also be noted that the first liquid and the second liquid may also be other liquids, such as disinfectant, soapy water, salt water, and soda water.

Referring to FIG. 3, the liquid path structure 20 may further comprise a drainage channel 221, which selectively communicates with at least one of the first functional mechanism 211 and the second functional mechanism 212 and configured to communicate with (e.g., connected to) a clean water tank of the cleaning robot and/or a cleaning tank of the base station. The drainage channel 221 may be configured to replenish the clean water tank when the drainage channel 221 is fluidly connected to the clean water tank of a cleaning robot 250. The drainage channel 221 may be configured to replenish the cleaning tank when connected to the cleaning tank of the base station, and/or when the mop of the cleaning robot is cleaned in the cleaning tank.

It should be noted that the liquid in the first functional mechanism 211 can be discharged through the drainage channel 221, and liquid in the first functional mechanism 211 may be untreated water or the first liquid after the first treatment. The liquid in the second functional mechanism 212 can also be discharged through the drainage channel 221, and the liquid in the second functional mechanism 212 may be untreated water or the second liquid after the second treatment.

Referring to FIG. 3, the liquid path structure 20 may further comprise a first liquid outlet pipe 222, a second liquid outlet pipe 223, and a first gate 231. The first liquid outlet pipe 222 may be configured to communicate with (e.g., connected to) the first functional mechanism 211 and selectively communicate with the drainage channel 221. The second liquid outlet pipe 223 may be configured to communicate with the second functional mechanism 212 and selectively communicate with the drainage channel 221. The first gate 231 may be connected to the first liquid outlet pipe 222, the second liquid outlet pipe 223, and/or the drainage channel 221. The first gate 23 may be configured to control the connection between the first liquid outlet pipe 222 and the drainage channel 221 and control the connection between the second liquid outlet pipe 223 and the drainage channel 221.

The first liquid outlet pipe 222 may be configured to discharge the liquid in the first functional mechanism 211. When the first liquid outlet pipe 222 communicates with the drainage channel 221, the first functional mechanism 211 communicates with the drainage channel 221. The second liquid outlet pipe 223 may be configured to discharge the liquid in the second functional mechanism 212. When the second liquid outlet pipe 223 communicates with the drainage channel 221, the second functional mechanism 212 communicates with the drainage channel 221. By connecting the first liquid outlet pipe 222 and the second liquid outlet pipe 223 with the drainage channel 221, the liquid in the first functional mechanism 211 and the liquid in the second functional mechanism 212 can be discharged simultaneously or separately. For example, if the first liquid is electrolyzed water and the second liquid is hot water, the liquid discharged from the drainage channel 221 may be water, electrolyzed water, hot water, or a mixture of electrolyzed water and hot water. The first gate 231 may be a device with a gating function. The first gate 231 can make the first liquid outlet pipe 222 and the second liquid outlet pipe 223 communicate with the drainage channel 221 through different channels separately, so that the first functional mechanism 211 and the second functional mechanism 212 may not interfere with each other.

Referring to FIG. 3, the liquid path structure 20 may further comprise a first water inlet pipe 224, a second water inlet pipe 225, a water supply pipe 226, and a second gate 232. The first water inlet pipe 224 may be configured to communicate with the first functional mechanism 211, and the second water inlet pipe 225 may be configured to communicate with the second functional mechanism 212. The water supply pipe 226 may be configured to selectively communicate with the first water inlet pipe 224 and the second water inlet pipe 225, and may be configured to provide the liquid for the first functional mechanism 211 and the second functional mechanism 212. The second gate 232 may be connected with the water supply pipe 226, the first water inlet pipe 224 and the second water inlet pipe 225, and may be configured to control the connection between the water supply pipe 226 and the first water inlet pipe 224 and the connection between the water supply pipe 226 and the second water inlet pipe 225.

It should be noted that the water supply pipe 226 can provide the liquid (e.g., water) for the first functional mechanism 211 or the second functional mechanism 212 separately, and can provide the liquid for the first functional mechanism 211 and the second functional mechanism 212 at the same time. When the first functional mechanism 211 needs to be replenished with water, the water supply pipe 226 communicates with the first water inlet pipe 224, so that the water supply pipe 226 communicates with the first functional mechanism 211. When the second functional mechanism 212 needs to be replenished with water, the water supply pipe 226 communicates with the second water inlet pipe 225, so that the water supply pipe 226 communicates with the second functional mechanism 212. The second gate 232 may be a device with a gating function. The second gate 232 can make the first water inlet pipe 224 and the second water inlet pipe 225 communicate with the water supply pipe 226 through different channels, so that the first functional mechanism 211 and the second functional mechanism 212 may not interfere with each other.

It can be understood that the water supply pipe 226 can communicate with a water source to convey (e.g., transport) the liquid provided by the water source to the first functional mechanism 211 and the second functional mechanism 212. The water source may be a water source on the base 10 or an external water source which is independent of the base 10, such as tap water.

It should also be noted that the second gate 232 may be a device with a gating function. The second gate 232 can make the first water inlet pipe 224 and the second water inlet pipe 225 communicate with the water supply pipe 226 separately through different channels, and the first gate 231 can make the first liquid outlet pipe 222 and the second liquid outlet pipe 223 communicate with the drainage channel 221 separately through different channels. By setting of (e.g., including) the second gate 232 and the first gate 231, the first functional mechanism 211 and the second functional mechanism 212 may not interfere with each other.

For example, if the first liquid is electrolyzed water and the second liquid is hot water, when the cleaning robot only needs electrolyzed water, the second gate 232 controls the water supply pipe 226 to communicate with the first water inlet pipe 224, and disconnect the water supply pipe 226 from the second water inlet pipe 225. The liquid then enters the first functional mechanism 211 and is treated by the first functional module to form electrolyzed water. The first gate 231 controls the first liquid outlet pipe 222 to communicate with the drainage channel 221, and disconnect the second liquid outlet pipe 223 from the drainage channel 221. The electrolyzed water in the first functional mechanism 211 may be discharged through the drainage channel 221. In another example, when the cleaning robot only needs hot water, the second gate 232 controls the water supply pipe 226 to be disconnected from the first water inlet pipe 224, and controls the water supply pipe 226 communicates with the second water inlet pipe 225, which cause the liquid to enter the second first functional mechanism 212 and is treated by the second functional module to form hot water. The first gate 231 may control the second liquid outlet pipe 223 to communicate with the drainage channel 221, and disconnect the first liquid outlet pipe 222 from the drainage channel 221. The hot water in the second functional mechanism 212 may be discharged through the drainage channel 221. When the cleaning robot needs a mixed liquid of hot water and electrolyzed water, the second gate 232 controls the water supply pipe 226 to communicate with the first water inlet pipe 224 and the second water inlet pipe 225, which causes the liquid to enter the first functional mechanism 211 and the second functional mechanism 212. The first gate 231 controls the first liquid outlet pipe 222 and the second liquid outlet pipe 223 to communicate with the drainage channel 221, and the electrolyzed water in the first functional mechanism 211 is mixed with the hot water in the second functional mechanism 212 in the drainage channel 221.

The second gate 232 and the first gate 231 may be a multi-channel solenoid valve, and pipes such as the water supply pipe 226, the first water inlet pipe 224 and the drainage channel 221 may be connected with interfaces of the multi-channel solenoid valve respectively to realize a gating function. The multi-channel solenoid valve has a gating function, so that the first functional mechanism 211 and the second functional mechanism 212 may not interfere with each other by switching a connection state of each channel. Only one multi-channel solenoid valve can realize a multiway communication function, thus reducing the number of valves, reducing costs, and realizing electric control and improving a response capability. The number of channels of the multi-channel solenoid valve can be selected according to actual needs, so that the first functional mechanism 211 and the second functional mechanism 212 may not interfere with each other.

The second gate 232 and the first gate 231 may also comprise one or more water pumps independent of each other. For example, the second gate 232 may comprise a first water pump and a second water pump which are independent of each other. The first water pump may be connected with the water supply pipe 226 and the first water inlet pipe 224, and the second water pump may be connected with the water supply pipe 226 and the second water inlet pipe 225. The liquid in the water supply pipe 226 may be pumped to the first water inlet pipe 224 by the first water pump, and the liquid in the water supply pipe 226 may be pumped to the second water inlet pipe 225 by the second water pump. Similarly, the first gate 231 may also comprise a third water pump and a fourth water pump which are independent of each other. The third water pump may be connected with the first liquid outlet pipe 222 and the drainage channel 221, and the fourth water pump may be connected with the second liquid outlet pipe 223 and the drainage channel 221. The liquid in the first liquid outlet pipe 222 may be pumped to the drainage channel 221 by the third water pump, and the liquid in the second liquid outlet pipe 223 may be pumped to the drainage channel 221 by the fourth water pump.

Referring to FIG. 3, the liquid path structure may further comprise a water storage tank 214 installed on the base 10, which has a water storage cavity 214a configured to store the liquid. The water storage tank 214 has a water storage function, and can provide the liquid for the first functional mechanism 211 and the second functional mechanism 212.

The first functional mechanism 211 has a first cavity 211a, the second functional mechanism 212 has a second cavity 212a, and the water storage cavity 214a may be configured to selectively communicate with the first cavity 211a and the second cavity 212a and can provide the liquid for the first cavity 211a and the second cavity 212a.

The water storage cavity 214a can communicate with the water supply pipe 226, and the water storage tank 214 can provide the liquid for the first cavity 211a and the second cavity 212a through the water supply pipe 226. The water storage tank 214 can also provide the liquid for the first cavity 211a and the second cavity 212a through another pipeline.

It can be understood that the water storage tank 214 is an independent mechanism from the first functional mechanism 211 and the second functional mechanism. For example, the first functional mechanism may comprise an electrolyzed water tank installed on the base 10, which comprises a first cavity 211a and a first functional module installed therein; the second functional mechanism may comprise a hot water tank installed on the base 10, which comprises a second cavity 212a and a second functional module installed therein, that is, the base 10 has three water tanks of the water storage tank 214, an electrolyzed water tank, and a hot water tank.

Figure 4:
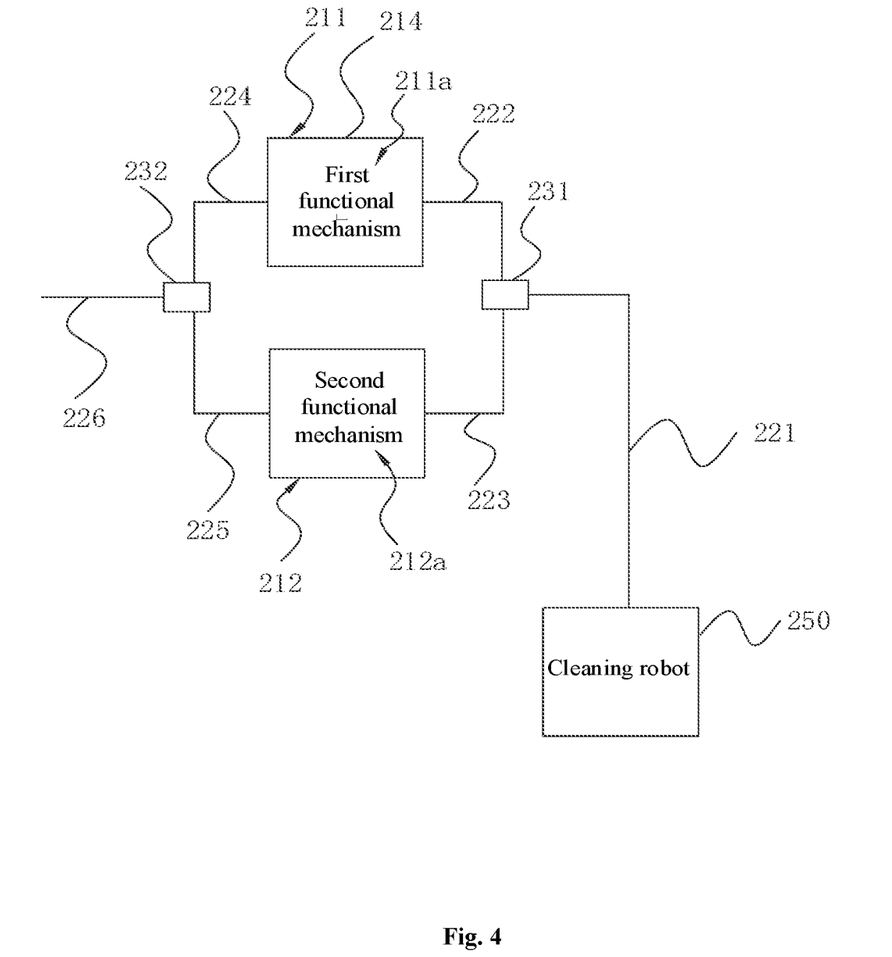
FIG. 4 shows a schematic diagram of a liquid path structure.

As shown in FIG. 4, the water storage tank 214 may comprise one of the first functional module and the second functional module. The water storage cavity 214a may comprise the first cavity 211a or the second cavity 212a. Besides the water storage function, the water storage tank 214 may have a function of heating water or electrolyzing water, without additionally setting a water tank such as an electrolyzed water tank or a hot water tank in the base 10.

It should also be noted that FIG. 4 only indicates an example in which the first functional mechanism 211 and the second functional mechanism 212 are connected to the drainage channel 221 in parallel, and the first functional mechanism 211 and the second functional mechanism 212 are isolated from each other.

Figure 5:
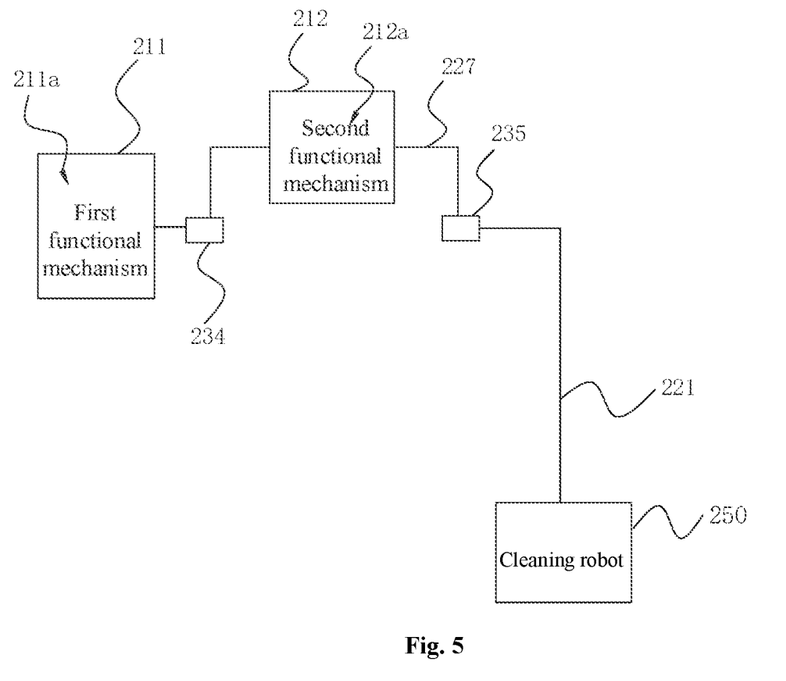
FIG. 5 shows a schematic diagram of a liquid path structure.

As shown in FIG. 5, the first functional mechanism 211 can also be connected in series with the second functional mechanism 212. The liquid path structure 20 may further comprise a third liquid outlet pipe 227 which is configured to communicate with the second functional mechanism 212 and selectively communicate with the drainage channel 221.

It should be noted that when the cleaning robot only needs water, both the first functional module and the second functional module may be closed (e.g., not activated to perform any function, not used), and then the water may be discharged through the first functional mechanism 211, the second functional mechanism 212, the third liquid outlet pipe 227, and the drainage channel 221 sequentially. The first functional mechanism 211, the second functional mechanism 212 may function as a bypass device for the fluids to pass to next device. When the cleaning robot only needs the first liquid, the first functional module is opened (e.g., activated to perform a function, used) and the second functional module is closed, after the first treatment on the liquid in the first functional mechanism 211, the first functional module may discharge the first liquid into the second functional mechanism 212, while the second functional module is in a closed state. The second functional module does not treat the first liquid in the second functional mechanism 212. Then the first liquid in the second functional mechanism 212 is discharged into the drainage channel 221 through the third liquid outlet pipe 227. When the cleaning robot only needs the second liquid, the first functional module is closed and the second functional module is opened, the liquid in the first functional mechanism 211 is discharged into the second functional mechanism 212, and then the second functional module performs the second treatment on the liquid in the second functional mechanism 212 to form the second liquid, and then the second liquid in the second functional mechanism 212 is discharged into the drainage channel 221 through the third drainage channel 221.

It can be understood that the first functional mechanism 211 can perform the first treatment on the liquid with the first functional module to form the first liquid, while a device such as a valve may or may not be disposed between the first functional mechanism 211 and the second functional mechanism 212.

The first functional mechanism 211 may also be used as a water storage container without setting (e.g., including) an additional water storage tank 214, thereby reducing the number of water tanks in the base station, while a device such as a valve can be set between the first functional mechanism 211 and the second functional mechanism 212 to cause the first functional mechanism 211 to selectively communicate with the second functional mechanism 212.

A first valve 234 may be set between the first functional mechanism 211 and the second functional mechanism 212 to realize selective communication between the first functional mechanism 211 and the second functional mechanism 212; a second valve 235 may be set between the third liquid outlet pipe 227 and the drainage channel 221 to realize selective communication between the third liquid outlet pipe 227 and the drainage channel 221. Both the first valve 234 and the second valve 235 may be a solenoid valve.

Figure 6:
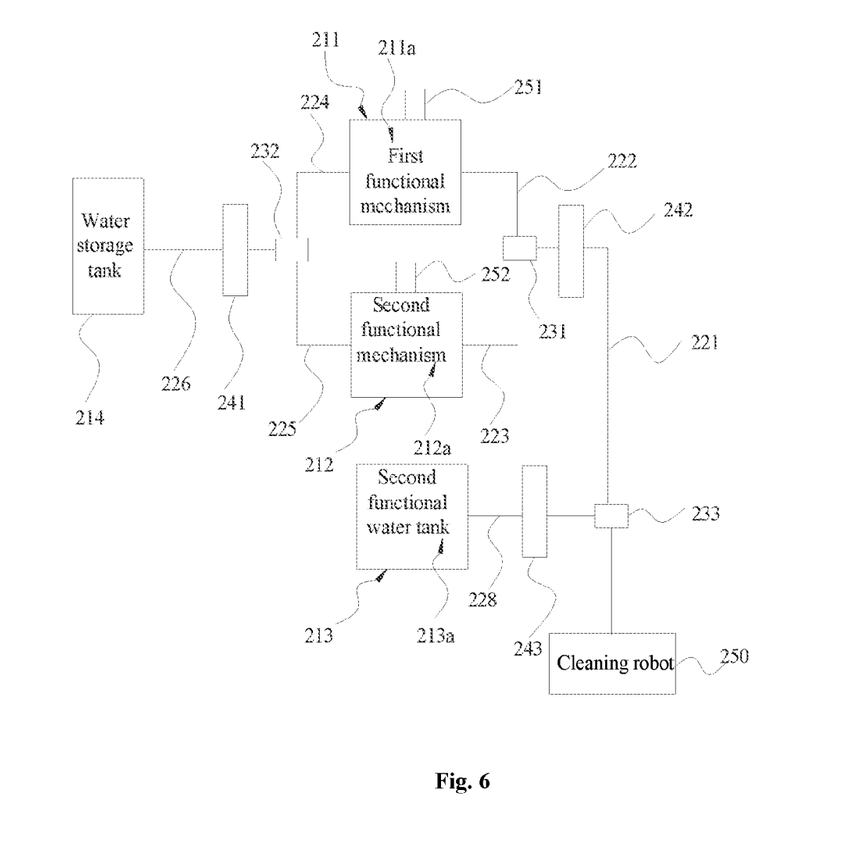
FIG. 6 shows a schematic diagram of a liquid path structure.

As shown in FIG. 6, the liquid path structure 20 may further comprise a second functional water tank 213 having a third cavity 213a in which a functional liquid is stored, the functional liquid being different in composition from the first liquid and the second liquid. A fourth liquid outlet pipe 228 may be configured to communicate with the third cavity 213a and selectively communicate with the drainage channel 221.

It should be noted that there may be some functional liquids that are difficult to be formed by water treatment among liquids needed by the cleaning robot when mopping the floor. The second functional water tank 213 may be installed on the base 10, and the functional liquid needed by the cleaning robot may be pre-stored in the third cavity 213a (or in the first cavity 211a and/or the second cavity 212a). When the functional liquid in the third cavity 213a is needed, the functional liquid in the third cavity 213a is introduced into the drainage channel 221 through the fourth liquid outlet pipe 228. It should also be noted that the functional liquid may comprise a cleaning liquid such as disinfectant, soapy water, salt water or soda water.

As shown in FIG. 6, the drainage channel 221 may only comprise a first drainage pipe and a second drainage pipe, and the liquid path structure 20 may further comprise a third gate 233. The first drainage pipe may be connected with the first gate 231 and the third gate 233, and the fourth drainage pipe and the second drainage pipe may be connected with the third gate 233, and the third gate 233 may be configured to control the connection between the fourth liquid outlet pipe 228 and the second drainage pipe and the connection between the first drainage pipe and the second drainage pipe.

The drainage channel 221 may also comprise only one drainage pipe, the fourth liquid outlet pipe 228 may selectively communicate with the drainage pipe, and a valve for controlling connection of the fourth liquid outlet pipe 228 may be provided on the fourth liquid outlet pipe 228.

Referring to FIG. 6 again, in order to facilitate conveyance of liquid in each water tank in the liquid path structure 20, the liquid path structure 20 may further comprise a first driver 241, a second driver 242, and a third driver 243.

The first driver 241 may be connected with a liquid supply pipe, the first water inlet pipe 224, and the second water inlet pipe 225, and may be configured to convey the liquid in the liquid supply pipe to the first water inlet pipe 224 and the second water inlet pipe 225. The second driver 242 may be connected with the first liquid outlet pipe 222, the second liquid outlet pipe 223, and the drainage channel 221, and may be configured to convey the liquid in the first cavity 211a to the drainage channel 221 and convey the liquid in the second cavity 212a to the drainage channel 221. The third driver 243 may be connected with the fourth liquid outlet pipe 228 and the drainage channel 221, and is configured to convey the liquid in the third cavity 213a to the drainage channel 221. The first driver 241, the second driver 242 and the third driver 243 may be water pumps.

According to actual needs, the liquid path structure 20 may not comprise a driver such as a water pump, but by designing height positions of the first functional mechanism 211, the second functional mechanism, 212 and the second functional water tank 213, the liquid in each water tank is smoothly conveyed to a designated place by a driving force generated by a height difference.

The base station may further comprise a selector and a control module. The selector may be in communication connection with the control module and configured to accept selection operation and output selection information according to the selection operation. The control module may be configured to control on/off of the first functional module and/or the second functional module according to the selection information. The control module can control on/off of the first functional module and the second functional module in the liquid path structure 20, so as to control the liquid path structure 20 to discharge a preset liquid which may be one of water, the first liquid, and the second liquid, or a mixed liquid of at least two of water, the first liquid, and the second liquid. The control module and the selector may be both installed on the base 10, and a user can control the liquid path structure 20 to discharge a required liquid in the base station: the selector may be a key selector or a knob selector. If the selector is a key selector, the selector may comprise a plurality of keys. A user may press the corresponding key to perform selection operation, thus controlling the liquid path structure 20 to discharge the required liquid. The control module can realize full-automatic liquid path control, and a user can meet liquid needs of the cleaning robot with one key through a simple interactive interface. The control module and the selector can be connected by wired connection or wireless connection (e.g., via a user's mobile phone).

The base station may further comprise a control module configured to be in communication connection with a terminal and receive the selection information sent by the terminal and control on/off of the first functional module and/or the second functional module according to the selection information.

The terminal may be a mobile phone, a tablet computer, a notebook computer, a personal digital assistant, a smart band, a smart watch or the like, and a user can control the liquid path structure 20 to discharge the required liquid in the terminal. The control module and the terminal can be connected by wired connection or wireless connection.

Referring to FIG. 6, if the first liquid is electrolyzed water, the second liquid is hot water, and the functional liquid is a cleaning liquid, an exemplary process of outputting various liquids by the liquid path structure 20 is described below: when the cleaning robot only needs water, the first driver 241 pumps water in the water storage tank 214 to the first functional mechanism 211. At this time, an electrolyzer in the first functional mechanism 211 is in an off state, then the second driver 242 pumps the water in the first functional mechanism 211 to the drainage channel 221, and the water is discharged into the cleaning robot through the drainage channel 221. When the cleaning robot only needs water, the first driver 241 may pump water in the water storage tank 214 to the second functional mechanism 212. At this time, a heater in the second functional mechanism 212 is in an off state, then the second driver 242 pumps the water in the second functional mechanism 212 to the drainage channel 221, and the water is discharged into the cleaning robot through the drainage channel 221.

When the cleaning robot only needs electrolyzed water, the first driver 241 pumps water in the water storage tank 214 to the first functional mechanism 211, an electrolyzer in the first functional mechanism 211 is in an on state, and the water in the first functional mechanism 211 is electrolyzed by the electrolyzer to form electrolyzed water. Then the second driver 242 pumps the electrolyzed water in the first functional mechanism 211 to the drainage channel 221, and the electrolyzed water is discharged into the cleaning robot through the drainage channel 221.

When the cleaning robot only needs hot water, the first driver 241 pumps water in the water storage tank 214 to the second functional mechanism 212, and the heater in the second functional mechanism 212 is in an on state. The water in the second functional mechanism is heated by the heater to form hot water, then the second driver 242 pumps the hot water in the second functional mechanism 212 to the drainage channel 221, and the hot water is discharged into the cleaning robot through the drainage channel 221.

When the cleaning robot needs electrolyzed water mixed with a cleaning liquid, the first driver 241 pumps water in the water storage tank 214 to the first functional mechanism 211. An electrolyzer in the first functional mechanism 211 is in an on state, and the water in the first functional mechanism 211 is electrolyzed by the electrolyzer to form electrolyzed water. Then the second driver 242 pumps the electrolyzed water in the first functional mechanism 211 to the drainage channel 221. At the same time, the third driver 243 pumps the cleaning liquid in the second functional water tank 213 into the drainage channel 221 to mix the cleaning liquid with electrolyzed water, and the electrolyzed water mixed with the cleaning liquid is discharged into the cleaning robot through the drainage channel 221.

When the cleaning robot needs hot water mixed with a cleaning liquid, the first driver 241 pumps water in the water storage tank 214 to the second functional mechanism 212. The heater in the second functional mechanism 212 is in an on state, and the water in the second functional mechanism 212 is heated by the heater to form hot water. Then the second driver 242 pumps the hot water in the second functional mechanism 212 to the drainage channel 221. At the same time, the third driver 243 pumps the cleaning liquid in the second functional water tank 213 into the drainage channel 221 to mix the cleaning liquid with hot water, and the hot water mixed with the cleaning liquid is discharged into the cleaning robot through the drainage channel 221.

Referring to FIG. 6, the first functional mechanism 211 may be provided with a first cavity 211a and a first vent hole 251 communicating with the first cavity 211a. The second functional mechanism 212 may be provided with a second cavity 212a and a second vent hole 252 communicating with the second cavity 212a.

It can be understood that the first vent hole 251 can make the first cavity 211a communicate with the atmosphere (e.g., air), thus preventing a siphon effect when the liquid in the first cavity 211a is discharged through the drainage pipe. Similarly, the second vent hole 252 can make the second cavity 212a communicate with the atmosphere, thus preventing a siphon effect when the liquid in the second cavity 212a is discharged through the drainage pipe.

When the second driver 242 pumps the liquid in the first cavity 211a and the liquid in the second cavity 212a to the drainage channel 221, a separating function can be added in the second driver 242, and when the second driver 242 is not working, the first and second drainage pipes 222 and 223 can be disconnected from the drainage channel 221.

The base station may further comprise liquid level detectors which are arranged in the first cavity 211a and the second cavity 212a and are configured to detect a level of the liquid in the first cavity 211a and a level of the liquid in the second cavity 212a.

It can be understood that the liquid level detector can detect the liquid level of the first cavity 211a and the second cavity 212a in real time, so as to avoid damage to the base station caused by continuous operation of the first functional mechanism 211 and the second functional mechanism 212 when being full or empty.

The liquid level detector may be a floating ball measuring detector, a tuning fork vibration measuring detector, an ultrasonic measuring detector, a laser measuring detector, a photoelectric refracting measuring detector, a photoelectric refracting measuring detector, or a capacitive measuring detector. Specific operating principles of the various liquid level detectors have been introduced in the related art and will not be repeated in the disclosure. It can be understood that when the base station further comprises a water tank such as the second functional water tank 213 which may also be provided with a liquid level detector, the liquid level detector can detect a liquid level in each water tank.

It should also be noted that the liquid level detector may be connected with the control module by wired connection or wireless connection, and the liquid level detector detects the liquid level in each water tank in real time and sends a detection signal to the control module, so that the control module can control each water tank to stop working in time when the water tank is full or empty, and replenish or drain each water tank.

Based on the above base station, the disclosure further provides a cleaning system comprising a cleaning robot and the base station of any one of the above examples configured to replenish or/and clean the cleaning robot.

The cleaning robot may be a sweeping robot, a sweeping and mopping robot, a hand-held vacuum cleaner, a hand-propelled cleaner or a driving cleaner, and the disclosure is not specifically limited. The cleaning robot may have a cleaning water tank, and the base station may replenish the cleaning water tank with liquids with various functions. The cleaning robot may also have a mop, and the base station may clean the mop.

The above are only examples of the present disclosure and are not intended to limit the disclosure. Any modifications, equivalent substitutions, improvements or the like within the spirit and principle of the disclosure should be included in the scope of the disclosure.

What is claimed is:

1. A cleaning base station for a cleaning robot comprising:
   a base; and
   a liquid path system disposed on the base, wherein the liquid path system comprises:
     a first device configured to perform a first treatment on water to form a first liquid;
     a second device configured to perform a second treatment on water to form a second liquid, wherein the second liquid is different from the first liquid;
     a drainage channel configured to selectively connect to one of the first device or the second device, and configured to connect to a first water tank of a cleaning device; and
     a liquid outlet pipe connected to the drainage channel and a second water tank of the cleaning base station,
   wherein the second water tank is configured to store a third liquid different in composition from the first liquid and the second liquid.

2. The cleaning base station according to claim 1, wherein the liquid path system further comprises:
   a first liquid outlet pipe connected to the first device and the drainage channel;
   a second liquid outlet pipe connected to the second device and the drainage channel; and
   a valve connected to the first liquid outlet pipe, the second liquid outlet pipe, and the drainage channel and configured to control connection between the first liquid outlet pipe and the drainage channel and control connection between the second liquid outlet pipe and the drainage channel.

3. The cleaning base station according to claim 1, wherein the liquid path system further comprises:
   a first water inlet pipe connected to the first device;
   a second water inlet pipe connected to the second device;
   a water supply pipe selectively connected to at least one of the first water inlet pipe and the second water inlet pipe and configured to provide water for at least one of the first device and the second device; and
   a valve connected to the water supply pipe.

4. The cleaning base station according to claim 1, wherein the first device and the second device are connected in series.

5. The cleaning base station according to claim 1, wherein the liquid comprises one of disinfectant, soapy water, salt water, or soda water.

6. The cleaning base station according to claim 1, wherein the liquid path system further comprises a water storage tank installed on the base, wherein the water storage tank is configured to store water.

7. The cleaning base station according to claim 6, wherein the first device comprises a first cavity, the second device comprises a second cavity, and the first water storage tank is selectively connected to with the first cavity or the second cavity.

8. The cleaning base station according to claim 6, wherein the first water storage tank comprises at least one of the first device or the second device.

9. The cleaning base station according to claim 1, wherein the first device comprises an electrolyzer configured to electrolyze water, and the second device comprises a heater configured to heat water.

10. The cleaning base station according to claim 1, wherein the first device comprises a first cavity and a first vent hole connected to the first cavity, and the second device comprises a second cavity and a second vent hole connected to the second cavity.

11. The cleaning base station according to claim 1, wherein the base station further comprises a selector and a control circuit, wherein:
    the selector is configured to receive an indication of a selection, and the control circuit is configured to control, based on the indication of selection, a state of at least one of the first device or the second device.

12. The cleaning base station according to claim 1, wherein the base station further comprises a control circuit configured to:
receive an indication of selection from a user device, and
control, based on the indication of selection, a state of at least one of the first device or the second device.

13. The cleaning base station according to claim 1, wherein the second liquid is of a different composition of liquid than the first liquid.

14. The cleaning base station according to claim 1, wherein the second liquid is of a same composition as the first liquid and has a different temperature than the first liquid.

15. A cleaning base station for a cleaning robot comprising:
a first water storage tank;
a second water storage tank;
a first device, in fluid communication with the first water storage tank, configured to perform a first treatment process on water;
a second device, in fluid communication with the first water storage tank, configured to perform a second treatment process on water, wherein the second treatment process is different from the first treatment process;
a drainage channel configured to selectively connect to one of the first device or the second device, and configured to connect to the first water storage tank;
a first fluid outlet pipe, in fluid communication with both the first and second devices, configured to fluidly couple with the cleaning robot; and
a second fluid outlet pipe connected to the drainage channel and the second water storage tank,
wherein the second water storage tank is configured to store a third liquid different in composition from a first liquid generated by the first treatment process and a second liquid generated by the second treatment process.

16. The cleaning base station according to claim 15, wherein the first device and the second device are connected in series or in parallel.

17. A cleaning base station for a cleaning robot comprising:
a first water storage tank;
a second water storage tank; and
a liquid path system connected to water storage tank, wherein the liquid path system is configured to:
form, based on a user instruction, a mixture of at least two different types of liquids, wherein a first liquid of the at least two different types of liquids is formed by a first device, and a second liquid of the at least two different types of liquids is formed by a second device; and
discharge the mixture of at least two different types of liquids to a cleaning device;
a drainage channel configured to selectively connect to one of the first device or the second device, and configured to connect to the first water storage tank; and
a liquid outlet pipe connected to the drainage channel and the second water storage tank,
wherein the second water storage tank is configured to store a liquid different in composition from the mixture of at least two different types of liquids.

* * * * *